US012678115B2

(12) United States Patent
Regensburger et al.

(10) Patent No.: US 12,678,115 B2
(45) Date of Patent: Jul. 14, 2026

(54) METHOD FOR GENERATING A VOLUME MODEL OF AN OBJECT UNDER EXAMINATION, CONTROL DEVICE, X-RAY APPARATUS, COMPUTER PROGRAM, AND ELECTRONICALLY READABLE DATA MEDIUM

(71) Applicant: Siemens Healthineers AG, Forchheim (DE)

(72) Inventors: Alois Regensburger, Poxdorf (DE); Michael Manhart, Fürth (DE)

(73) Assignee: Siemens Healthineers AG, Forchheim (DE)

( * ) Notice: Subject to any disclaimer, the term of this patent is extended or adjusted under 35 U.S.C. 154(b) by 263 days.

(21) Appl. No.: 18/648,693

(22) Filed: Apr. 29, 2024

(65) Prior Publication Data

US 2024/0374227 A1 Nov. 14, 2024

(30) Foreign Application Priority Data

May 9, 2023 (DE) ..................... 10 2023 204 265.7

(51) Int. Cl.
  *G06V 10/00* (2022.01)
  *A61B 6/00* (2006.01)
  (Continued)

(52) U.S. Cl.
  CPC ............ *A61B 6/482* (2013.01); *A61B 6/4085* (2013.01); *G06T 7/62* (2017.01); *G06T 12/10* (2026.01); *G06V 10/44* (2022.01)

(58) Field of Classification Search
  CPC ...... G06V 10/44; G06V 10/82; G06V 10/761; G06V 10/762; G06V 10/764;
  (Continued)

(56) References Cited

U.S. PATENT DOCUMENTS 8,855,395 B2 * 10/2014 Baturin ................ A61B 6/5217
                                                    378/62
9,380,984 B2 * 7/2016 Li .......................... A61B 6/032
              (Continued)

FOREIGN PATENT DOCUMENTS

JP        2008012027 A    1/2008
JP        2011177396 A    9/2011
              (Continued)

OTHER PUBLICATIONS

Clark, Darin P., et al. "Deep learning based spectral extrapolation for dual-source, dual-energy x-ray computed tomography." Medical physics 47.9 (2020): 4150-4163.
              (Continued)

*Primary Examiner* — Amir Alavi
(74) *Attorney, Agent, or Firm* — Lempia Summerfield Katz LLC

(57) ABSTRACT

A method is provided for generating a volume model of an object under examination from a data set that includes first 2D projection images created in a first X-ray spectrum and second 2D projection images created in a second X-ray spectrum. The method includes: supplementing the 2D projection images with fill projections and reconstructing a preliminary volume model from the supplemented 2D projection images; determining a spectral X-ray absorption property of at least one volume element and generating virtual 2D projection images from the preliminary volume model as a function of the spectral X-ray absorption property of the at least one volume element; and reconstructing the volume model from the virtual 2D projection images and/or the supplemented 2D projection images and the virtual 2D projection images.

16 Claims, 3 Drawing Sheets

(51) Int. Cl.

| | | |
|---|---|---|
| *A61B 6/40* | (2024.01) | |
| *G06T 7/62* | (2017.01) | |
| *G06T 12/10* | (2026.01) | |
| *G06V 10/44* | (2022.01) | |

(58) Field of Classification Search

CPC .. G06V 10/765; G06V 10/7715; A61B 6/482; A61B 6/5211; A61B 6/032; A61B 6/4085; G06T 7/62; G06T 2211/441; G06T 2211/408; G06T 12/20; G06T 12/10

See application file for complete search history.

(56) References Cited

U.S. PATENT DOCUMENTS

| | | | | |
|---|---|---|---|---|
| 9,554,766 | B2 * | 1/2017 | Kyriakou | A61B 6/5258 |
| 9,888,896 | B2 * | 2/2018 | Lauritsch | A61B 6/5288 |
| 10,762,647 | B2 * | 9/2020 | Buerger | G06T 7/33 |
| 12,033,406 | B2 * | 7/2024 | Bae | G06V 20/647 |
| 12,236,600 | B2 * | 2/2025 | Lavi | G06T 7/0014 |
| 12,499,549 | B2 * | 12/2025 | Conjeti | G06T 7/11 |

| | | | | |
|---|---|---|---|---|
| 2009/0087055 | A1 * | 4/2009 | Maltz | G06T 12/10 |
| | | | | 382/131 |
| 2020/0170590 | A1 | 6/2020 | Gagnon et al. | |
| 2024/0374227 | A1 * | 11/2024 | Regensburger | A61B 6/482 |

FOREIGN PATENT DOCUMENTS

| | | |
|---|---|---|
| JP | 2022509680 A | 1/2022 |
| WO | 2014181889 A1 | 11/2014 |

OTHER PUBLICATIONS

Huang, Yixing, et al. "Data extrapolation from learned prior images for truncation correction in computed tomography." IEEE transactions on medical imaging 40.11 (2021): 3042-3053.

Liu, Chi-Kuang, and Hsuan-Ming Huang. "Unsupervised deep learning based image outpainting for dual-source, dual-energy computed tomography." Radiation Physics and Chemistry 188 (2021): 109635. pp. 1-7.

Maaß, Nicole, et al. "Empirical multiple energy calibration (EMEC) for material-selective CT." 2011 IEEE Nuclear Science Symposium Conference Record. IEEE, 2011. pp. 1-8.

* cited by examiner

METHOD FOR GENERATING A VOLUME MODEL OF AN OBJECT UNDER EXAMINATION, CONTROL DEVICE, X-RAY APPARATUS, COMPUTER PROGRAM, AND ELECTRONICALLY READABLE DATA MEDIUM

The present patent document claims the benefit of German Patent Application No. 10 2023 204 265.7, filed May 9, 2023, which is hereby incorporated by reference in its entirety.

TECHNICAL FIELD

The disclosure relates to a method for generating a volume model of an object under examination. The disclosure further relates to a control device, an X-ray apparatus, a computer program, and an electronically readable data medium.

BACKGROUND

Cone beam computed tomography (CBCT) and limited-angle tomography are imaging methods for generating a reconstruction image of an object under examination.

In both methods, X-ray radiation is emitted by an X-ray source onto the object under examination, wherein a main beam area opens up from the X-ray source. In cone beam computed tomography, the main beam area is conical. Opposite the X-ray source is a flat-panel detector, which detects the transmitted X-rays as a two-dimensional projection image of the object under examination. The object under examination is arranged between the X-ray source and the flat-panel detector. To enable the reconstruction of a reconstruction image of the object under examination, a data set is captured that includes multiple 2D projection images of the object under examination.

To capture the 2D projection images of the object under examination for the data set, the X-ray source and the flat-panel detector are moved along a mostly circular trajectory around the object under examination. The respective 2D projection images of the object under examination are generated in respective positions along the trajectory. As a result, the data set includes multiple 2D projection images that map the object under examination in different orientations. The 2D projection images of the data set are processed in accordance with a predetermined reconstruction method in order to generate a reconstruction image of the object under examination.

For an optimum reconstruction of the object under examination in cone beam computed tomography (CBCT), it is necessary for the object under examination to be penetrated by the X-ray beams in each of the positions. In other words, it is necessary for the entire object under examination to be located inside the conical main beam area during the capture of the respective projection image.

A special type of cone beam computed tomography (CBCT) is dual-energy cone beam computed tomography (DE-CBCT). In this, 2D projection images with two different X-ray spectra are captured from the object under examination.

The 3D reconstruction and spectral evaluation of the 2D projection images from dual-energy cone beam computed tomography is made significantly more difficult due to a number of effects. Among other things, these include scattered radiation, beam hardening, metal artifacts, and cupping artifacts.

However, a particular challenge arises if a truncation occurs in the 2D projection images for dual-energy cone beam computed tomography. Truncation means that parts of the patient or of the object under examination are not recorded from the complete angular range required for the 3D reconstruction, so that only insufficient information for a reconstruction is provided about these parts of the patient.

For ordinary cone beam computed tomography using just a single recording spectrum, there are a plurality of known approaches to correction to cope with the truncation and the reconstruction artifacts connected thereto. However, spectral effects in particular are not taken into account in these models, resulting in reconstruction artifacts in the models from dual-energy cone beam computed tomography.

The basic problem in limited-angle tomography is that the 2D projection images are recorded only over a limited angular range. As a result, reconstruction artifacts may likewise arise during the reconstruction.

The following methods are known from the prior art in this field, which however are not directed at the above-mentioned problem.

The publication by Clark, Darin P., et al. (Clark, Darin P., et al. "Deep learning based spectral extrapolation for dual-source, dual-energy x-ray computed tomography." Medical physics 47.9 (2020): 4150-4163) describes an approach for dual-energy fan beam CT based on a deep-learning method. This publication relates to a dual-energy CT scanner that has a larger image reconstruction volume for a first X-ray spectrum than for a second X-ray spectrum. In this case, a complete 3D reconstruction is available for the first spectrum, whereas a truncation takes place for the second spectrum. A 3D reconstruction of the second X-ray spectrum is predicted based on the 3D reconstruction of the first X-ray spectrum with the help of a neural network.

The publication by Huang, Yixing, et al. (Huang, Yixing, et al. "Data extrapolation from learned prior images for truncation correction in computed tomography." IEEE Transactions on Medical Imaging 40.11 (2021): 3042-3053) describes a method for correcting a truncation. However, this correction is not directed at cases in which two X-ray spectra are used.

SUMMARY AND DESCRIPTION

It is an object of the disclosure to provide a solution for compensating for a truncation for tomography methods which capture projection images using at least two X-ray spectra. The object is in particular to provide a solution for dual-energy cone beam computed tomography and limited-angle tomography.

The scope of the present disclosure is defined solely by the appended claims and is not affected to any degree by the statements within this summary. The present embodiments may obviate one or more of the drawbacks or limitations in the related art.

One approach of the disclosure is to create a truncation model of the object under examination with spectral properties and/or an assumed material composition from 2D projection images of a measurement for dual-energy cone beam computed tomography or limited-angle tomography.

A first aspect of the disclosure relates to a method for generating a volume model of an object under examination from a data set.

The data set includes first 2D projection images of an object under examination captured in a first X-ray spectrum from the object under examination. The data set furthermore includes second 2D projection images of the object under examination captured in a second X-ray spectrum from the object under examination. In other words, the data set includes the 2D projection images that separately map the object under examination in the two X-ray spectra. The X-ray spectra may include different energy spectra.

The 2D projection images each map a projection volume of the object under examination that is arranged in a field of view of the respective 2D projection images. In other words, a respective one of the 2D projection images includes a respective object projection that maps the projection volume of the object under examination. The respective projection volume is a partial volume of a total volume of the object under examination. The projection volume is the volume that, during the creation of the respective 2D projection image, is arranged in the respective field of view of the X-ray apparatus. The projection volume of the 2D projection image is identical to the total volume of the object under examination if, during the acquisition of the 2D projection image in question, the object under examination is located completely in the field of view of the X-ray apparatus. If the object under examination is not located completely inside the field of view, only the part of the total volume of the object under examination inside the field of view is mapped by the 2D projection image in question. In this case, the projection volume does not include the complete total volume. The 2D projection image in question is thus missing areas that would map the part of the total volume outside the projection volume. Because the total volume of the object under examination is not captured in the 2D projection image in question, there is a lack of information for the reconstruction of the area not captured. This area is referred to as the truncation volume. In contrast, the part of the total volume that, during each acquisition of the 2D projection image, was located inside the respective field of view is referred to as a primary capture area.

The method includes acts executed by a control device.

A first act of the method includes receipt of the data set from an X-ray apparatus by the control device. The X-ray apparatus may be an apparatus for the performance of a CT examination that has created the 2D projection images of the object under examination.

In a following act, the 2D projection images are supplemented. Supplementing includes expanding at least one truncated 2D projection image of the first 2D projection images and/or one truncated 2D projection image of the second 2D projection images with a fill projection. The fill projection maps a fill volume of the object under examination arranged outside the field of view of the at least one truncated 2D projection image.

The fill volume is a part of the object under examination arranged outside the respective field of view of the respective 2D projection image. In other words, it is a part of the total volume of the object under examination located outside the projection volume mapped by the 2D projection image. To be able to take into account the parts of the total volume in the respective 2D projection images not covered by the projection volume, the individual 2D projection images are supplemented by the fill projections. In other words, individual 2D projection images are supplemented and/or extrapolated in order to compensate for missing areas that arise because the object under examination is not arranged completely in the field of view. Thus, not all of the 2D projection images need be supplemented, but only those in which part of the object under examination is truncated.

One act of the method entails reconstructing a preliminary volume model of the object under examination from the supplemented 2D projection images. In other words, the supplemented 2D projection images, including the at least one expanded truncated 2D projection image, are used for the reconstruction of the preliminary volume model of the object under examination. The reconstruction may take place in accordance with a customary reconstruction method in accordance with the prior art.

A further act entails determining a spectral X-ray absorption property of at least one volume element, wherein the at least one volume element is arranged inside the fill volume of the at least one truncated 2D projection image. In other words, the at least one volume element is located inside a truncation volume of the preliminary volume model. The spectral X-ray absorption property is determined as a function of the supplemented 2D projection images.

A following act entails generating virtual 2D projection images of the object under examination for both the X-ray spectra from the preliminary volume model of the object under examination. The virtual 2D projection images are generated as a function of the spectral X-ray absorption property of the at least one volume element. In other words, a virtual examination of the object under examination is performed by the control device. As a result, the virtual 2D projection images of the preliminary volume model are generated. When generating the virtual 2D projection images, the spectral X-ray absorption property of the at least one volume element is taken into account. In other words, an absorption of beams of the X-ray spectra dependent on the X-ray absorption property of the at least one volume element may be simulated.

A following act entails reconstructing the volume model of the object under examination from the virtual 2D projection images or from the supplemented 2D projection images and the virtual 2D projection images. In this case, a known reconstruction method in accordance with the prior art may be applied. The reconstruction may be based solely on the virtual 2D projection images. Alternatively, the reconstruction may be based on the supplemented 2D projection images and the virtual 2D projection images. In certain examples, virtual 2D projection images may be used for areas of the object under examination that were not irradiated by the captured 2D projection images.

The disclosure has the advantage that a truncation in dual-energy cone beam computed tomography may be compensated for.

In certain examples, the volume model of the object under examination includes a single-energy volume model of the object under examination for the first X-ray spectrum and a single-energy volume model of the object under examination for the second X-ray spectrum. In other words, the volume model includes two separate single-energy volume models of the respective X-ray spectra. The single-energy volume model of the object under examination for the first X-ray spectrum is reconstructed from the virtual 2D projection images, generated in the first X-ray spectrum, or generated from the supplemented first 2D projection images. In other words, the single-energy volume model of the object under examination for the first X-ray spectrum is reconstructed from the virtual 2D projection images generated for the first X-ray spectrum. Alternatively, the reconstruction takes place from the first projection images and the virtual 2D projection images generated for the first X-ray spectrum. It is accordingly provided that the single-energy volume model of the object under examination for the second X-ray spectrum is reconstructed from the virtual 2D projection images, generated in the second X-ray spectrum, or generated from the supplemented second 2D projection images. In other words, the single-energy volume model of the object under examination for the second X-ray spectrum is reconstructed from the virtual 2D projection images generated for the second X-ray spectrum. Alternatively, the reconstruction takes place from the second projection images and the virtual 2D projection images generated for the second X-ray spectrum.

In certain examples, the volume model of the object under examination includes a dual-energy volume model of the object under examination for both X-ray spectra. In other words, a dual-energy volume model is generated that characterizes the object under examination in both X-ray spectra. The dual-energy volume model of the object under examination for both X-ray spectra is reconstructed from the virtual 2D projection images generated in both X-ray spectra, or from the supplemented first 2D projection images and the supplemented second 2D projection images.

In certain examples, the supplementing the 2D projection images entails a deep-learning method. In other words, the deep-learning method is used to supplement the 2D projection images with the fill projections. It may be provided that an artificial neural network, on which the deep-learning method is based, is trained on 2D projection images and/or volume models of objects in a category of the object under examination. As a result, it is possible to reconstruct the truncated areas of the object under examination based on known objects. One method is disclosed in the publication by Huang, Yixing, et al. (Huang, Yixing, et al. "Data extrapolation from learned prior images for truncation correction in computed tomography." IEEE Transactions on Medical Imaging 40.11 (2021): 3042-3053). For example, the truncated 2D projection image together with further information on the object under examination may be fed to the artificial neural network as input data. In addition, further of the 2D projection images may be provided as input data. The neural network may reproduce the truncated 2D projection image supplemented with the fill projection as output data.

In certain examples, the supplementing the 2D projection images entails providing the fill projections from a specified standard model of the object under examination. In other words, a standard model for the object under examination is provided that is used to supplement the fill projections. The standard model may be a water cylinder model. When generating the fill projections, it may be assumed that the object under examination is arranged in a cylinder volume made of water.

In certain examples, the method includes reconstructing the preliminary volume model of the object under examination from the non-supplemented 2D projection images. In other words, before generating the preliminary volume model from the supplemented 2D projection images, the preliminary volume model is generated from the non-supplemented 2D projection images. This has the advantage that the 2D projection images may be supplemented by including a non-truncated volume of the preliminary volume model.

In certain examples, the method includes identifying a material in at least one partial area of one of the 2D projection images based on a model of the partial area. In other words, an identification method is performed for the at least one partial area of the 2D projection images in order to identify the material of the partial area. Models that are assigned to different materials may be stored in a database of the control device. A material of a bone may be distinguished from soft tissue by a characteristic structure of the model. The respective spectral absorption properties may be assigned to the material in the database. As a result, the spectral absorption properties of the at least one volume element may be determined based on the material.

In certain examples, the method includes identifying a partial object volume of at least one partial object of the object under examination in the preliminary volume model. In other words, the preliminary volume model is examined for the presence of the partial object volume.

In a following act, the partial object volume in the preliminary volume model is supplemented as a fill volume. In other words, part of the partial object volume may be located outside the primary capture area so that a complete reconstruction of the partial object volume from the non-supplemented 2D projection images is not possible. By identifying the partial object, a partial object volume of the partial object may be retrieved from the database and the partial object volume may be supplemented in the volume model.

In certain examples, the method entails identifying image features of the at least one partial object of the object under examination in the 2D projection images. In other words, in the 2D projection images, those image features are identified that are assigned to the partial object of the object under examination. The image feature may be an outline, an edge, or a point of the partial object. The image feature may be identified in the 2D projection images by the control device by image recognition methods. The control device may be provided with a database that may describe the partial object and/or the image features of the partial object.

In a following act, a position of the partial object volume of the at least one partial object in the volume model of the object under examination is ascertained as a function of positions of the respective image features of the at least one partial object in the 2D projection images. In other words, the image features of the at least one partial object are identified in the respective 2D projection images of the object under examination and the respective position thereof in the projection image is determined. The position of the partial object in the volume model is determined from the positions of the image features assigned to the respective partial object.

In certain examples, the at least one volume element is arranged inside the truncated partial object volume and the determination of the spectral X-ray absorption property of the at least one volume element includes retrieving the spectral X-ray absorption property of the partial object volume from a database. In other words, the spectral X-ray absorption properties may be stored for the partial object. The spectral X-ray absorption property of at least one area of the partial object volume that includes the at least one volume element may be retrieved from the database. The spectral X-ray absorption property may be assigned to the volume element.

In certain examples, the determination of the spectral X-ray absorption property of the at least one volume element includes the following acts. In one act, a surface element assigned to the at least one volume element in one of the first 2D projection images is identified. In other words, the surface element that for example maps the volume element in the first 2D projection image is identified. In another act, the surface element assigned to the at least one volume element in one of the second 2D projection images is identified. In other words, the surface element in the second 2D projection image is identified. As a result, it is possible to provide projection values, also called signal intensity values, which are captured in the surface element, to determine the X-ray absorption property of the volume element. In a following act, the spectral X-ray absorption property of the volume element is determined from the projection values of the surface element in the 2D projection images of both the X-ray spectra.

In certain examples, the method includes the following acts to be performed by the X-ray apparatus.

In an act, the first 2D projection images of the object under examination in the first X-ray spectrum are captured. In another act, the second 2D projection images of the object under examination in the second X-ray spectrum are captured. One act includes the provision of the data set, including the first 2D projection images and the second 2D projection images, to the control device.

In certain examples, the 2D projection images are generated in accordance with a dual-energy cone beam computed tomography method. The 2D projection images may be provided to the control device by an external X-ray apparatus. The 2D projection images may also be captured in the context of the method by the X-ray apparatus and provided to the control device.

In certain examples, the 2D projection images are generated in accordance with a limited-angle tomography method. The 2D projection images may be provided to the control device by an external X-ray apparatus. The 2D projection images may also be captured in the context of the method by the X-ray apparatus and provided to the control device.

In other words, the method is applied to 2D projection images from a limited-angle tomography method. In certain examples, additional information for limited-angle tomography may be generated if appropriate via multiple spectral calculations of projection images with the different X-ray spectra. The spectral information may be used as input data for model-based or iterative limited-angle tomography.

For individual applications or situations that may arise with the method and that are not explicitly described here, an error message and/or a request to input user feedback is output and/or a default setting and/or a predetermined initial state is set in accordance with the method.

A second aspect of the disclosure relates to a control device configured to generate a volume model of an object under examination from a data set.

The data set includes first 2D projection images of an object under examination, created in a first X-ray spectrum, and second 2D projection images of the object under examination, created in a second X-ray spectrum. The 2D projection images each map a projection volume of the object under examination arranged in a field of view of the respective 2D projection image. The control device is configured to receive the data set from an X-ray apparatus. The control device is configured to supplement the 2D projection images.

The control device is configured to supplement the 2D projection images, in that at least one truncated 2D projection image of the first 2D projection images and/or of the second 2D projection images is expanded by the control device with a fill projection. The fill projection maps a fill volume of the object under examination arranged outside the field of view of the at least one truncated 2D projection image.

The control device is configured to determine a spectral X-ray absorption property of at least one volume element that is arranged inside the fill volume of the at least one truncated 2D projection image as a function of the supplemented 2D projection images. The control device is configured to generate virtual 2D projection images of the X-ray spectra of the object under examination from the preliminary volume model of the object under examination as a function of the spectral X-ray absorption property of the at least one volume element. The control device is configured to reconstruct the volume model of the object under examination from the virtual 2D projection images or from the supplemented 2D projection images and the virtual 2D projection images.

The control device may contain one or more computers, one or more microcontrollers, and/or one or more integrated circuits, (e.g., one or more application-specific integrated circuits (ASIC), one or more field-programmable gate arrays (FPGA), and/or one or more systems on a chip (SoC)). The computing unit may also contain one or more processors, (e.g., one or more microprocessors), one or more central processing units (CPU), one or more graphics processing units (GPU), and/or one or more signal processors, (e.g., one or more digital signal processors (DSP)). The computing unit may also contain a physical or a virtual group of computers or other of the units mentioned.

A third aspect of the disclosure relates to an X-ray apparatus. The X-ray apparatus has at least one control device in accordance with the second aspect of the disclosure. The X-ray apparatus is configured to capture first 2D projection images of an object under examination, created in a first X-ray spectrum, and second 2D projection images of the object under examination, created in a second X-ray spectrum, wherein a respective one of the 2D projection images maps a respective object projection of a respective projection volume of the object under examination. The respective projection volume is a partial volume of a total volume of the object under examination that is arranged in a respective field of view of the respective 2D projection image. The X-ray apparatus is configured to provide a data set of the 2D projection images of the object under examination to the control device to generate a volume model of the object under examination.

A fourth aspect of the disclosure relates to a computer program that may be loaded directly into a memory of a control device, with program means for executing the acts of the above-mentioned method if the program is executed in the control device. The method described herein may therefore also be present in the form of a computer program product that implements the method on a control device if it is executed on the control device.

A fifth aspect of the disclosure relates to an electronically readable data medium with electronically readable control information stored thereon, which includes at least one described computer program and is configured such that when the data medium is used in a control device it performs a described method.

Further features of the disclosure emerge from the claims, the figures, and the description of the figures. The features and combinations of features mentioned above in the description as well as the features and combinations of features mentioned below in the description of the figures and/or shown in the figures may be included by the disclosure not only in the combination indicated in each case, but also in other combinations. In particular, embodiments and combinations of features may also be included by the disclosure that do not have all the features of an originally formulated claim. In addition, the disclosure may include embodiments and combinations of features that go beyond or deviate from the combinations of features set out in the back-references of the claims.

BRIEF DESCRIPTION OF THE DRAWINGS

The disclosure is explained in greater detail below using concrete embodiments and associated schematic drawings.

Identical or functionally identical elements may be provided with the same reference characters in the figures. The description of identical or functionally identical elements is likewise not necessarily repeated in respect of different figures. In the figures.

DETAILED DESCRIPTION

Figure 1:
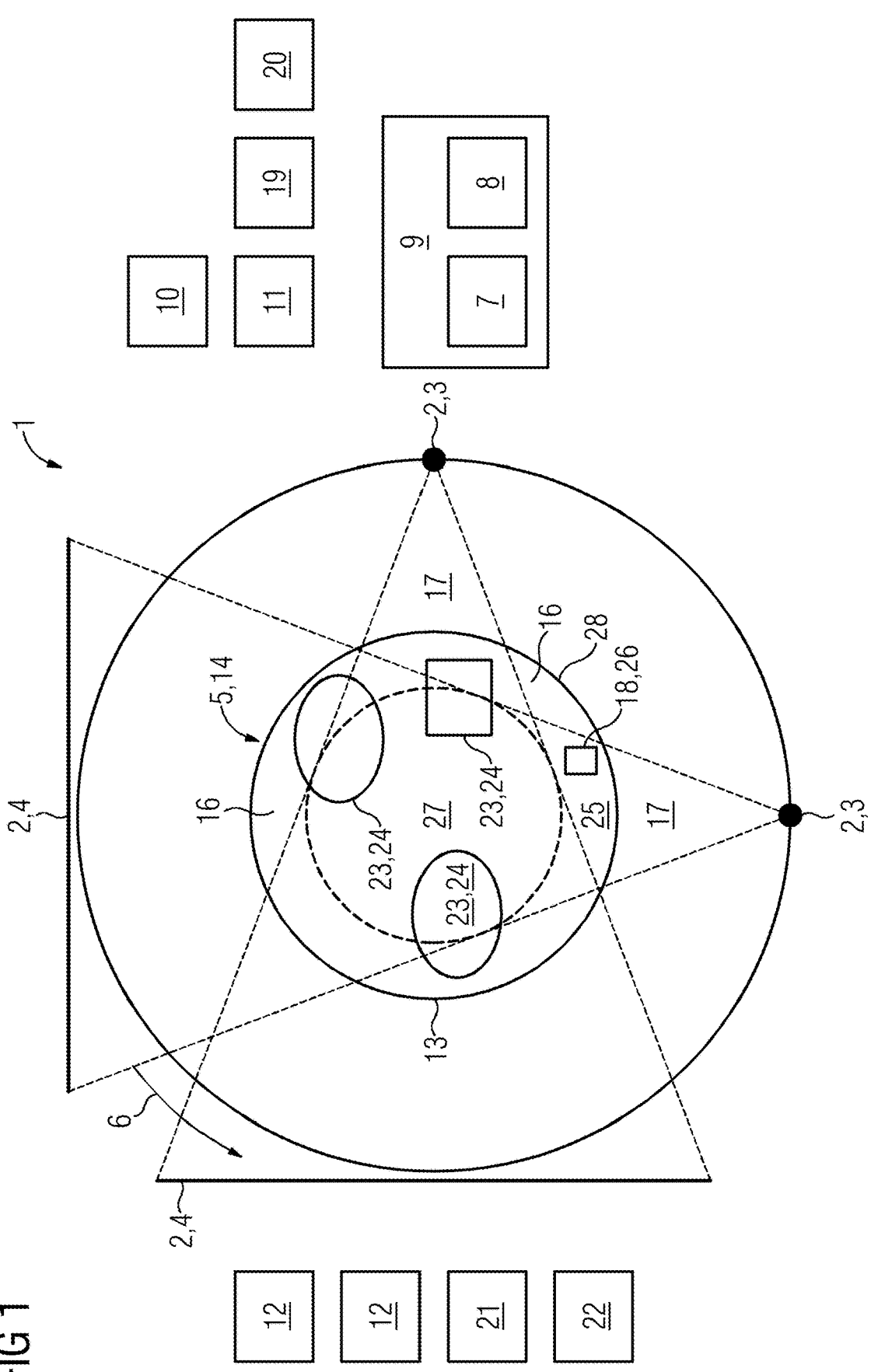
FIG. 1 shows a schematic representation of an example of a capture of 2D projection images of an object under examination by an X-ray apparatus.

FIG. 1 shows a schematic representation of a capture of 2D projection images of an object under examination by an X-ray apparatus.

The X-ray apparatus 1 may have an acquisition device 2 that may include an X-ray source 3 and an acquisition screen 4. The X-ray source 3 may be configured to emit X-ray beams along a conical volume toward the acquisition screen 4. The X-ray apparatus 1 may be configured for the performance of a dual-energy cone beam computed tomography method and/or a limited-angle tomography method. To this end, the X-ray apparatus 1 may output the X-ray beams in two different X-ray spectra.

An object under examination 5 may be arranged between the X-ray source 3 and the acquisition screen 4. The X-ray beams are absorbed by the object under examination 5 so that the acquisition screen 4 captures a two-dimensional projection image 7, 8 of the object under examination 5. The absorption of the X-ray beams in the object under examination 5 may depend on the X-ray spectrum of the X-ray beams. The X-ray beams of the first X-ray spectrum may be captured in first 2D projection images 7, and the X-ray beams of the second X-ray spectrum may be captured in second 2D projection images 8.

A reconstruction of a volume model 11 of the object under examination 5 requires an acquisition of a plurality of the 2D projection images 7, 8 of the object under examination 5 from different directions. For this, the X-ray apparatus 1 may be configured to move the X-ray source 3 and the acquisition screen 4 along a trajectory 6, (e.g., a circular trajectory 6), around the object under examination 5. In predetermined directions, the respective 2D projection images 7, 8 of the object under examination 5 may be captured in the respective X-ray spectrum and may be added to a data set 9. A control device 10 of the X-ray apparatus 1 may be configured to reconstruct the volume model 11 of the object under examination 5 from the first 2D projection images 7 and the second 2D projection images 8.

For a complete reconstruction of the volume model 11 of the object under examination 5, it is necessary for a total volume 14 of the object under examination 5 to be captured completely during a respective measurement. To this end, the total volume 14 is arranged inside the cone during each acquisition of the respective 2D projection images 7, 8 so that the object under examination 5 is irradiated completely, and the projection image 7, 8 includes the object under examination 5 over a total respective dimension. However, it may also be the case that, in at least some positions of the acquisition device 2, missing areas 28 of the object under examination 5 lie outside the cone and are thus not captured by the respective projection image 7, 8. In this case, there is a so-called truncation. As a result, errors may occur in the volume model 11 of the object under examination 5.

An area that is sufficiently irradiated is referred to as a primary reconstruction volume 27. The other area is referred to as a truncation volume 25. The truncation volume 25 may include the volumes that were located outside the field of view during at least one acquisition of one of the projection images 7, 8. For a reconstruction, it may be necessary to supplement the 2D projection images 7, 8 with fill projections 15. The control device 10 may be configured to supplement the 2D projection images 7, 8 with the fill projections 15 and/or to supplement a preliminary volume model 19 created from the non-supplemented 2D projection images 7, 8 with fill volumes 16. To supplement the fill projections 15, a standard model of the object under examination 5 may be assumed, which may map a water cylinder. In this case, the truncation volume 25 may be supplemented by a water cylinder as a fill volume 16.

Partial objects 23 may be arranged in the object under examination 5 and may have respective partial object volumes 24. The partial object volumes 24 may also be located partially inside the primary reconstruction volume 27 and partially outside the primary reconstruction volume 27. To generate the fill volume 16, image features 21 of the partial objects 23 may be identified in the 2D projection images 7, 8, and their positions determined in the 2D projection images 7, 8. From this, the control device 10 may determine a position of the partial object volume 24 of the partial object 23 in the volume model 11. The partial object volume 24 of the partial object 23 may be stored in a database of the control device 10. As a result, the control device 10 may identify the partial object 23 in the 2D projection images 7, 8 of the object under examination 5 based on the image features 21. Part of the partial object volume 24 in the truncation volume 25 that is not mapped in one of the 2D projection images 7, 8 may be supplemented as a fill projection 15 in the other projection image 7, 8. The missing part may be determined or estimated from the partial object volume 24 stored in the database.

The partial object volumes 24 may also be identified in a preliminary volume model 19 of the object under examination 5, which may be determined from the non-supplemented 2D projection images 7, 8. An X-ray absorption property may be determined for at least one volume element 18 of the preliminary volume model 11. The X-ray absorption property may be ascertained based on a material 22, which may be recognized based on a structure in a partial area of one of the 2D projection images 7, 8. The X-ray absorption property of the material 22 may be stored in a database of the control device 10.

After the preliminary volume model 11 is generated, virtual 2D projection images 20 may be created from the preliminary volume model 18 by the control device 10.

Figure 2:
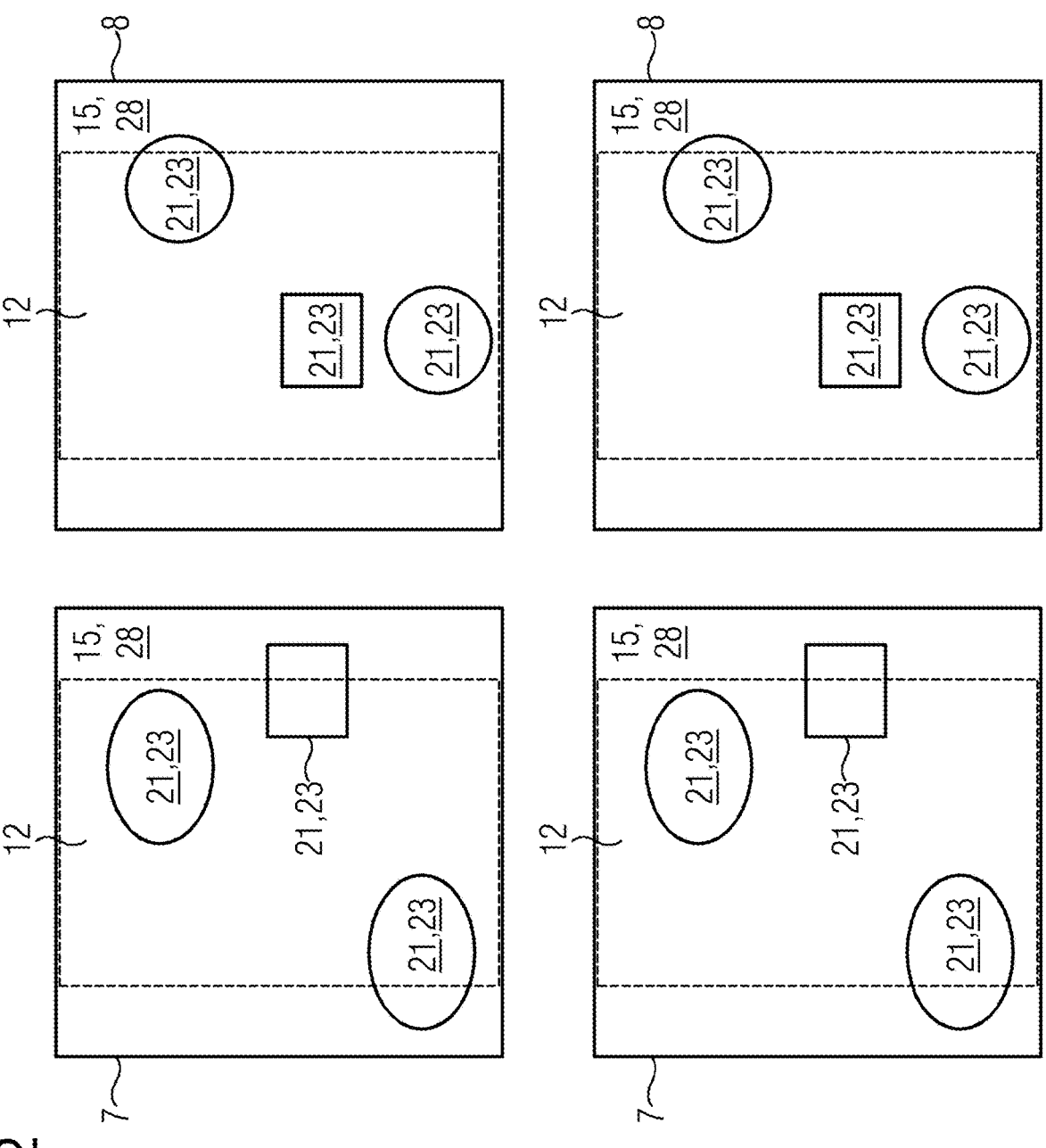
FIG. 2 shows a schematic representation of examples of 2D projection images of an object under examination.

FIG. 2 shows a schematic representation of 2D projection images 7, 8 of an object under examination 5.

The 2D projection images 7, 8 may have object projections 12 that map the projection volume 13 of the object under examination 5 of the respective measurement. The projection volume 13 may describe the part of the total volume 14 of the object under examination 5 located inside the cone and thus the field of view 17 of the respective measurement. The missing area 28 outside the object projection 12 may show the part of the 2D projection images 7, 8 that has been supplemented.

The 2D projection images 7, 8 of the object under examination 5 may be created from two positions for the respective X-ray spectra. Due to the X-ray absorption property of materials, intensity values of the 2D projection images 7, 8 may be distinguished from one another as a function of the X-ray spectrum. As a result, a material may be identified. The outlines of the partial objects 23 may represent the image features 21 of the partial objects 23 that may be identified by the control device 10. The position of the partial object 23 in the volume model 11 may be determined from the position of the image features 21.

Figure 3:
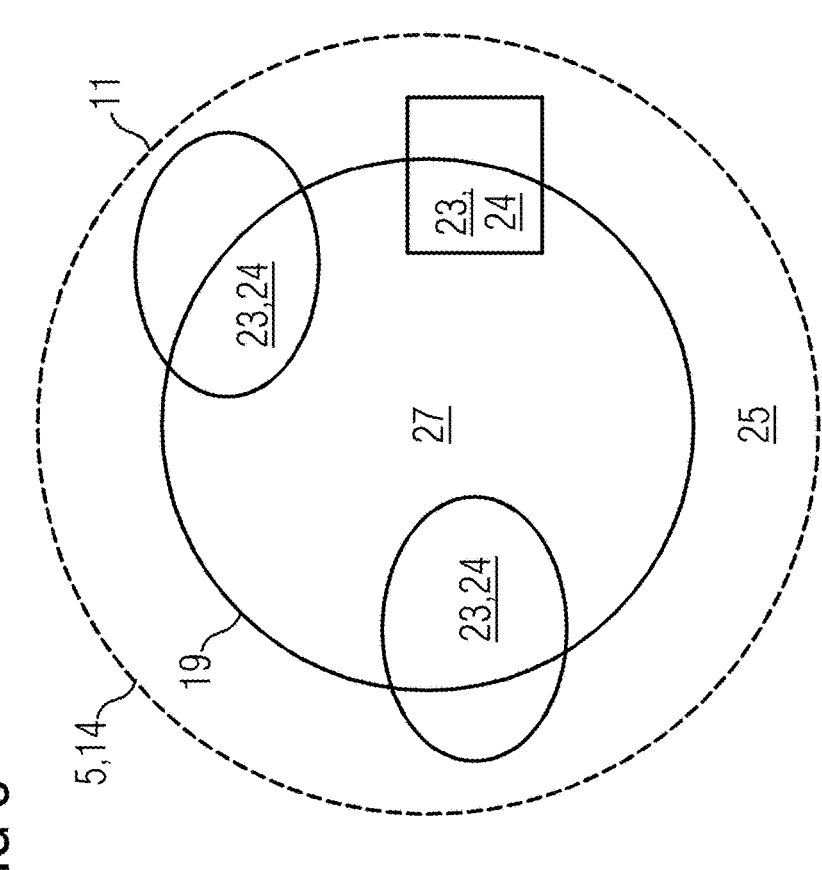
FIG. 3 shows a schematic representation of an example of a reconstructed volume model.

FIG. 3 shows a schematic representation of a reconstructed volume model 11.

The truncation volume 25 outside the primary reconstruction volume 27 may be supplemented by the fill volume 16. By way of example, a volume element 18 is shown whose X-ray absorption property is determined.

Figure 4:
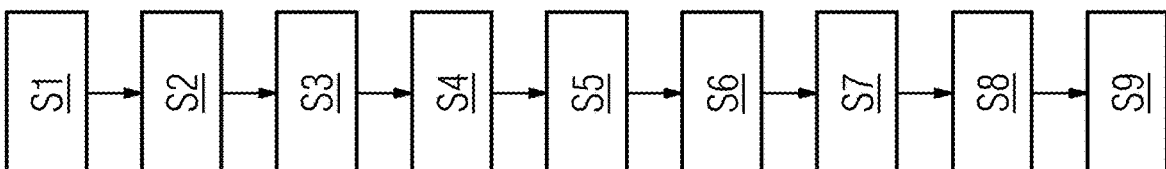
FIG. 4 shows a schematic representation of an example of an operational sequence of a method.

FIG. 4 shows a schematic representation of an operating sequence of a method.

In act S1, a DE-CBCT scan of an object under examination 5 may be performed by an X-ray apparatus 1. During the DE-CBCT scan, 2D projection images 7, 8 with a first and a second X-ray spectrum may be acquired. The DE-CBCT scan may be acquired using known dual-energy methods such as for example dual source, fast kV switching, fast filter switching, or dual layer & photon counting detectors. Both the X-ray spectra may be distinguished from one another in at least one wavelength range. A truncation may have occurred, as a result of which there are 2D projection images 7, 8 in which a missing area 28 of the object under examination 5, (e.g., a lateral area), is cut off. The cut-off missing area 28 may have been located outside the field of view 17 when the projection image 7, 8 was captured. The 2D projection images 7, 8 of the object under examination 5 of the X-ray spectra may be added to a data set 9 that may be provided to a control device 10 to generate a volume model 11.

In act S2, a first image reconstruction for the reconstruction of a preliminary volume model 19 may optionally be performed by the control device 10 by known acts in accordance with the prior art for the reconstruction of the primary reconstruction volume 27. The non-truncated area may describe the total volume 14 of the object under examination 5 in the primary reconstruction volume 27. The reconstruction may optionally take place separately for the 2D projection images 7 of the first X-ray spectrum and the 2D projection images 8 of the second X-ray spectrum. The truncation volume 25 shown in the 2D projection images 7, 8 of both the X-ray spectra may optionally be estimated using known methods for truncation correction.

In an optional act S3, if it is possible with the selected dual-energy acquisition technique, dual-energy 2D projection images 7, 8 may be calculated from corresponding 2D projection images 7, 8 of the respective X-ray spectra using a weighted subtraction or other methods of image calculation. If necessary, the corresponding 2D projection images 7, 8 may be combined in a motion-compensated manner.

In the dual-energy 2D projection images 7, 8, partial objects 23 such as bones or a contrast agent may be highlighted or alternatively also suppressed. For example, using a method described in the publication Maaß, Nicole, et al. "Empirical multiple energy calibration EMEC for material-selective CT," 2011 IEEE Nuclear Science Symposium Conference Record, material-specific projection values and/or X-ray absorption properties may be ascertained from the corresponding 2D projection images 7, 8 of the different X-ray spectra.

In act S4, sufficiently contrasted partial objects 23 and/or image features 21 may be segmented and/or detected in the 2D projection images 7, 8 or in dual-energy 2D projection images derived from the respective 2D projection images 7, 8. The partial objects 23 may be bones, the surface of the skin, accumulations of contrast agent such as contrasted vessels, implants, external objects, or organs. Image features 21, such as landmarks, of the partial objects 23 may be captured in the 2D projection images 7, 8. A whole partial object volume 24 of a partial object 23 or at least one part of the partial object volume 24 may be captured.

The partial objects 23 may optionally be classified and/or assigned. For example, a type of bone may be identified as a left elbow using a known orientation of the patient on the couch headfirst supine. Using corresponding image features 21 that are captured in a number of the 2D projection images 7, 8, the position of the bone may be estimated. Analogously, the outlines of an arm, the surface of the body, implants, or other organs/objects of the patient may be determined in the truncation volume 25.

The detection may be supported by the spectral differences in the 2D projection images 7, 8. For example, the segmentation of the partial objects 23 may be done with convolutional neural networks, wherein the corresponding 2D projection images 7, 8 of the different X-ray spectra may be used as input values for the convolutional neural networks. As a result, the convolutional neural networks may differentiate more easily between partial objects 23, in particular overlapping partial objects 23.

For example, an anatomical partial object 23, (e.g., a bone or another partial object 23), may be highlighted by a 2D dual-energy calculation of the corresponding 2D projection images 7, 8, which corresponds to a projection image 7, 8 of both different X-ray spectra. This partial object 23 may lie outside the primary reconstruction volume 27 due to lateral detector truncation. Thanks to the dual-energy calculation, a detection and triangulation, or else limited-angle tomography of partial objects 23 in the truncation volume 25, may be enabled, and a material of these partial objects 23 may be ascertained or estimated. As a result, the truncation model for the patient may be improved.

In act S5, the 2D projection images 7, 8 may be extrapolated using deep-learning approaches as described in the publication by Huang, Yixing, et al. and/or by a standard model of the object under examination 5, for example, of a simple water cylinder model or of a patient model. The supplemented image areas, (e.g., fill projections 15), of the 2D projection images 7, 8 may then be aligned with the captured and/or supplemented image areas in the other 2D projection images 7, 8.

In act S6, the preliminary volume model 19 may be supplemented by a partial object volume 24 of a captured partial object 23. For example, if the bone or a section of a bone or another detected partial object 23 lies at least partly in the truncation volume 25, the position of this bone and/or its outlines may be adjusted in the volume model 11 and/or this partial object volume 24 may be added anew to the volume model 19, if it is not yet present in at least one area of the volume model 19.

In act S7, the reconstruction of the primary reconstruction volume 27, and, via the fill projections 15 added in the 2D projection images 7, 8 in the areas outside the primary reconstruction volume 27, the preliminary volume model 19 of the object under examination 5 may be present in an area that is relevant to imaging. Spectral X-ray absorption properties of the at least one volume element 18 of the preliminary volume model 19 may be determined in the truncated areas based on the previously performed classifications of the partial objects 23.

In act S8, virtual 2D projection images 20 of the preliminary volume model 19 may be generated. In the first and the second X-ray spectrum, the missing areas 28 of the respective virtual 2D projection images 20 may be supplemented with respect to the 2D projection images 7, 8.

In act S9, a separate reconstruction of the volume model 11 may be performed separately for both X-ray spectra, taking into account the virtual 2D projection images 20. Alternatively, a shared reconstruction of the volume model 11 for both X-ray spectra may be performed in order to reconstruct the volume model 11 as a dual-energy reconstruction image. The reconstruction may be performed by the virtual 2D projection images 20 alone. Alternatively, the reconstruction may be performed by the supplemented 2D projection images 7, 8 and the virtual 2D projection images 20. In certain examples, the supplemented 2D projection images 7, 8 may be supplemented at least partly with the virtual 2D projection images 20. This may be done at edges of the field of view in order to expand the field of view by the virtual 2D projection images 20. As a result, truncations at the edge of the object under examination 5 may be prevented.

The volume model 11 extracted from the 2D projection images 7, 8 of the dual-energy CBCT method may also be used for further correction acts, taking account of material properties. The correction acts may include a scattered radiation correction and/or a metal artifact correction. The correction acts may also be used during an interventional procedure, for example to determine a dosage distribution on the patient.

It is to be understood that the elements and features recited in the appended claims may be combined in different ways to produce new claims that likewise fall within the scope of the present disclosure. Thus, whereas the dependent claims appended below depend on only a single independent or dependent claim, it is to be understood that these dependent claims may, alternatively, be made to depend in the alternative from any preceding or following claim, whether independent or dependent, and that such new combinations are to be understood as forming a part of the present specification.

While the present disclosure has been described above by reference to various embodiments, it may be understood that many changes and modifications may be made to the described embodiments. It is therefore intended that the foregoing description be regarded as illustrative rather than limiting, and that it be understood that all equivalents and/or combinations of embodiments are intended to be included in this description.

The invention claimed is:

1. A method for generating a volume model of an object under examination from a data set, wherein the data set comprises first two-dimensional (2D) projection images of the object under examination created in a first X-ray spectrum and second 2D projection images of the object under examination created in a second X-ray spectrum, and wherein the first 2D projection images and the second 2D projection images each map a projection volume of the object under examination arranged in a field of view of the respective 2D projection images, the method comprising:

receiving, by a control device, the data set from an X-ray apparatus;

supplementing, by the control device, the first 2D projection images and the second 2D projection images, comprising an expansion of at least one truncated 2D projection image of the first 2D projection images and/or of the second 2D projection images with a fill projection, wherein the fill projection maps a fill volume of the object under examination arranged outside the field of view of the at least one truncated 2D projection image;

reconstructing, by the control device, a preliminary volume model of the object under examination from the supplemented 2D projection images;

determining, by the control device, a spectral X-ray absorption property of at least one volume element of the preliminary volume model as a function of the supplemented 2D projection images, wherein the at least one volume element is arranged inside the fill volume of the at least one truncated 2D projection image;

generating, by the control device, virtual 2D projection images of the X-ray spectra of the object under examination from the preliminary volume model of the object under examination as a function of the spectral X-ray absorption property of the at least one volume element; and reconstructing, by the control device, the volume model of the object under examination from the virtual 2D projection images or from the supplemented 2D projection images and the virtual 2D projection images.

2. The method of claim 1, wherein the volume model of the object under examination comprises a single-energy volume model of the object under examination for the first X-ray spectrum and a single-energy volume model of the object under examination for the second X-ray spectrum, wherein the single-energy volume model of the object under examination for the first X-ray spectrum is reconstructed from the virtual 2D projection images generated in the first X-ray spectrum or from the supplemented first 2D projection images, and wherein the single-energy volume model of the object under examination for the second X-ray spectrum is reconstructed from the virtual 2D projection images generated in the second X-ray spectrum or from the supplemented second 2D projection images.

3. The method of claim 1, wherein the volume model of the object under examination comprises a dual-energy volume model of the object under examination for both X-ray spectra, and wherein the dual-energy volume model of the object under examination for both X-ray spectra is reconstructed from the virtual 2D projection images generated in both the first X-ray spectrum and the second X-ray spectrum or from the supplemented first 2D projection images and the supplemented second 2D projection images.

4. The method of claim 1, wherein the supplementing of the first 2D projection images and the second 2D projection images comprises using a deep-learning method.

5. The method of claim 1, wherein the supplementing of the first 2D projection images and the second 2D projection images comprises providing the fill projection from a specified standard model of the object under examination.

6. The method of claim 1, further comprising:

reconstructing, by the control device, the preliminary volume model of the object under examination from the first 2D projection images and the second 2D projection images.

7. The method of claim 1, further comprising:

identifying, by the control device, a material of at least one partial area of the first 2D projection images or the second 2D projection images based on a model of the partial area; and determining, by the control device, the spectral X-ray absorption property of the at least one volume element as a function of the material of the partial area.

8. The method of claim 1, further comprising:

identifying, by the control device, a partial object volume of at least one partial object of the object under examination in the preliminary volume model; and supplementing, by the control device, a truncated partial object volume as a fill volume in the preliminary volume model.

9. The method of claim 8, further comprising:

identifying, by the control device, image features of the at least one partial object of the object under examination in the first 2D projection images and the second 2D projection images; and ascertaining, by the control device, a position of the partial object volume of the at least one partial object in the preliminary volume model of the object under examination as a function of positions of the respective image features of the at least one partial object in the first 2D projection images and the second 2D projection images.

10. The method of claim 8, wherein the at least one volume element is arranged inside the truncated partial object volume, and wherein the determination of the spectral X-ray absorption property of the at least one volume element comprises retrieving the spectral X-ray absorption property of the partial object from a database.

11. The method of claim 1, wherein the determination of the spectral X-ray absorption property of the at least one volume element comprises:

identifying a surface element assigned to the volume element in one projection image of the first 2D projection images;

identifying the surface element assigned to the volume element in one projection image of the second 2D projection images; and determining the spectral X-ray absorption property of the volume element from projection values of the surface element in the first 2D projection images and the second 2D projection images.

12. The method of claim 1, further comprising:

capturing, by the X-ray apparatus, the first 2D projection images of the object under examination in the first X-ray spectrum;

capturing, by the X-ray apparatus, the second 2D projection images of the object under examination in the second X-ray spectrum; and providing, by the X-ray apparatus, the data set comprising the first 2D projection images and the second 2D projection images to the control device.

13. The method of claim 12, wherein the first 2D projection images and the second 2D projection images are captured by the X-ray apparatus in accordance with a dual-energy cone beam computed tomography method.

14. The method of claim 12, wherein the first 2D projection images and the second 2D projection images are captured by the X-ray apparatus in accordance with a limited-angle tomography method.

15. An X-ray device comprising:

a control device configured to:

receive a data set from an X-ray apparatus, wherein the data set comprises first 2D projection images of an object under examination created in a first X-ray spectrum and second 2D projection images of the object under examination created in a second X-ray spectrum, and wherein the 2D projection images each map a projection volume of the object under examination arranged in a field of view of the respective 2D projection image;

supplement the first 2D projection images and the second 2D projection images, wherein at least one truncated 2D projection image of the first 2D projection images and/or of the second 2D projection images is expanded with a fill projection, and wherein the fill projection maps a fill volume of the object under examination arranged outside the field of view of the at least one truncated 2D projection image;

reconstruct a preliminary volume model of the object under examination from the supplemented 2D projection images;

determine a spectral X-ray absorption property of at least one volume element arranged inside the fill volume of the at least one truncated 2D projection image as a function of the supplemented 2D projection images;

generate virtual 2D projection images of the first X-ray spectrum and the second X-ray spectrum of the object under examination from the preliminary volume model of the object under examination as a function of the spectral X-ray absorption property of the at least one volume element; and reconstruct a volume model of the object under examination from the virtual 2D projection images or the supplemented 2D projection images and the virtual 2D projection images.

16. A non-transitory electronically readable data medium with electronically readable control information stored thereon, which comprises at least one computer program and is configured such that, when the non-transitory electronically readable data medium is used in a control device, the control device is configured to:

receive a data set from an X-ray apparatus, wherein the data set comprises first 2D projection images of an object under examination created in a first X-ray spectrum and second 2D projection images of the object under examination created in a second X-ray spectrum, and wherein the 2D projection images each map a projection volume of the object under examination arranged in a field of view of the respective 2D projection image;

supplement the first 2D projection images and the second 2D projection images, wherein at least one truncated 2D projection image of the first 2D projection images and/or of the second 2D projection images is expanded with a fill projection, and wherein the fill projection maps a fill volume of the object under examination arranged outside the field of view of the at least one truncated 2D projection image;

reconstruct a preliminary volume model of the object under examination from the supplemented 2D projection images;

determine a spectral X-ray absorption property of at least one volume element arranged inside the fill volume of the at least one truncated 2D projection image as a function of the supplemented 2D projection images;

generate virtual 2D projection images of the first X-ray spectrum and the second X-ray spectrum of the object under examination from the preliminary volume model of the object under examination as a function of the spectral X-ray absorption property of the at least one volume element; and reconstruct a volume model of the object under examination from the virtual 2D projection images or the supplemented 2D projection images and the virtual 2D projection images.

* * * * *